Figure 2:
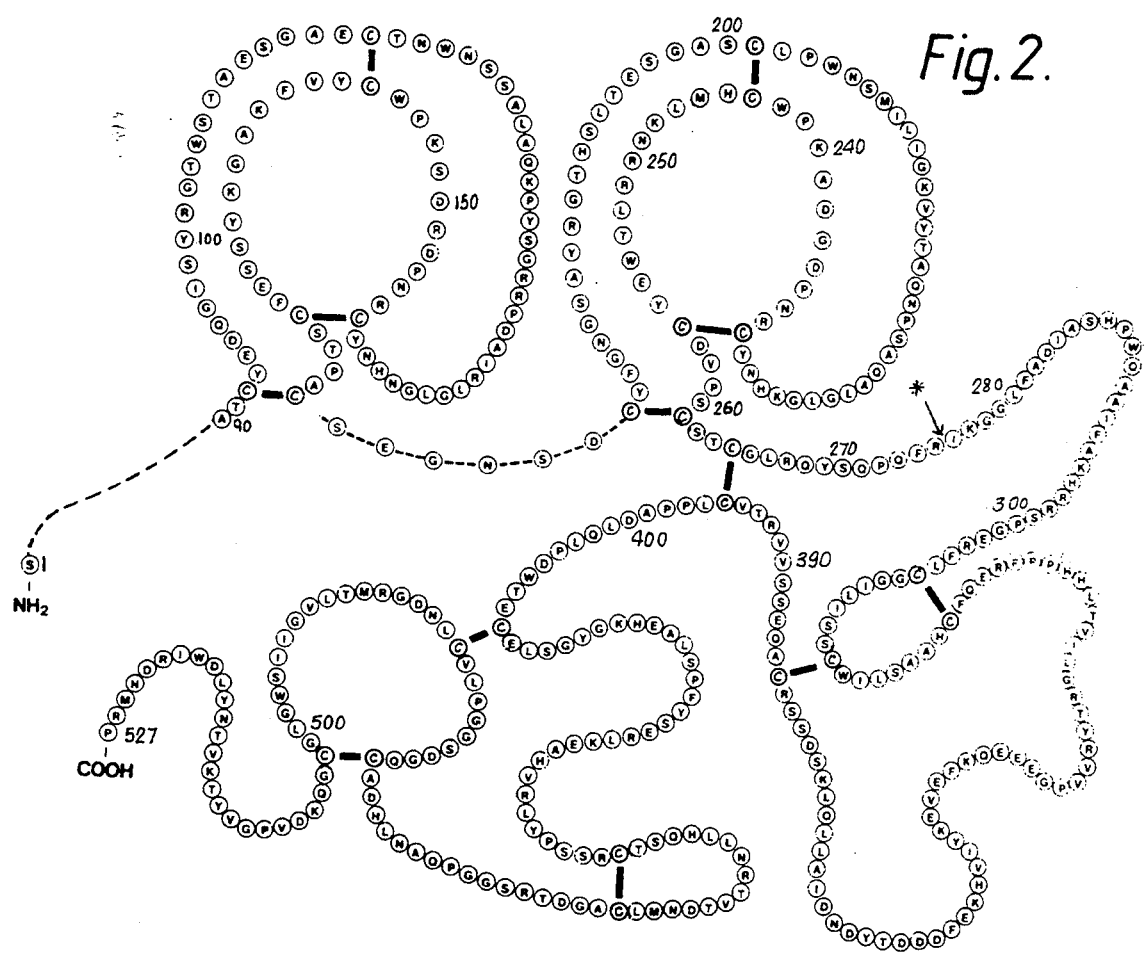

United States Patent [19]

Cohen

[11] Patent Number: 5,342,616

[45] Date of Patent: Aug. 30, 1994

[54] METHOD OF ADMINISTERING TISSUE PLASMINOGEN ACTIVATOR

[75] Inventor: Adam F. Cohen, EN Oegstgeest, Netherlands

[73] Assignee: The Wellcome Foundation Limited, London, England

[21] Appl. No.: 994,083

[22] Filed: Dec. 16, 1992

Related U.S. Application Data

[63] Continuation of Ser. No. 831,641, Feb. 7, 1992, abandoned, which is a continuation of Ser. No. 367,857, Jun. 19, 1989, abandoned.

[30] Foreign Application Priority Data

Jun. 20, 1988 [GB] United Kingdom .............. 8814604.8

[51] Int. Cl.$^5$ .......................................... A61K 37/547
[52] U.S. Cl. .................................................. 424/94.64
[58] Field of Search ....................................... 424/94.64

[56] References Cited

U.S. PATENT DOCUMENTS

| | | | |
|---|---|---|---|
| 4,772,585 | 9/1988 | Sarnoff et al. | 424/94.64 |
| 4,837,022 | 6/1989 | Kakimoto et al. | 424/94.64 |
| 4,839,169 | 6/1989 | Whittle | 424/94.64 |
| 4,935,237 | 6/1990 | Higgins et al. | 424/94.64 |
| 4,960,702 | 10/1990 | Rice et al. | 424/94.64 |
| 4,968,617 | 11/1990 | Johnston et al. | 424/94.64 |

FOREIGN PATENT DOCUMENTS

| | | |
|---|---|---|
| 252005 | of 0000 | European Pat. Off. . |
| 0211592 | 2/1987 | European Pat. Off. . |
| 218112 | 4/1987 | European Pat. Off. . |

OTHER PUBLICATIONS

Longridge et al., Cardiovascular Research, vol. 25:184–191 1991.
Hackett et al., Am. J. Cardiol. vol. 69:1393–1398 (Jun. 1, 1992).
Eisert et al., Blood, vol. 68, No. 5, suppl 1, p. 332a, 1208 Nov., 1986.
Gold et al., in Sobel et al., Editions, Tissue Plasminogen Activator in Thrombolytic Therapy, New York, 1987, Marcel Dekker, "Prevention of Acute Reocclusion After Thrombolysis with Intravenous Recombinant Tissue Plasminogen Activator" pp. 115–130.
Scand. J. Haematol., 1984 33, 49–53, Nilsson et al.
Blood, 1985, 66(2), 399–401, Agnelli et al.
Thrombosis Research, 1985, 40, 769–777, Agnelli et al.
Fifth Amstol Symposium, Amsterdam, 1986, pp. 1–14, Turpie.
Thrombosis and Haemostasis, 1987, 57(1), 35–40, Eisenberg et al.
Seminars in Thrombosis and Haemostasis, 1987, 13(2), 160–162, Agnelli et al.
J.A.C.C., 1987, 9(3), 599–607, Garabedian et al.
J.A.C.C., 1987 10(5), 16B–21B, Gurewich.
J. Cardiovasc. Pharmac., 1988 11, 468–472, Cambier et al.
Circulation, 1988, 77(3), 670–77, Gold et al.
Fibrinolysis, 1988, 2. Suppl, Abstract No. 2, Eiseret et al.
Thrombosis and Haemostasis, 1988 60(2), 271–179, Bloom et al.
Thrombosis Research, 1988, 52, 295–312, Badylak et al.
Circulation, 1989, 79(1), 125–133, Clozel et al.
Am. J. Cardiol., 1989, 64, 448–453, Tebbe et al.
The Lancet, Oct. 21, 1989, 989–990, Verstraete et al.
Brit. Heart J., 1989, 61, 453–4, Khan et al.
Eur. Heart J., 1989, 10th Supplement, 135, Khan et al.
Clinical Science, 1989, 76, Supplement, 135, Khan et al.
Coronary Artery Disease, 1990, 1, 83–88, Tranchesi et al.
World Congress of Cardiology, Manilla, Feb. 13, 1990, 22–23 Verstraete et al.

Primary Examiner—Jacqueline Stone
Attorney, Agent, or Firm—Nixon & Vanderhye

[57] ABSTRACT

The use of bolus injections of t-PA in the treatment of human beings with a thrombotic disorder.

8 Claims, 2 Drawing Sheets

Fig. 1.

Ser Tyr Gln Val Ile Cys Arg Asp Glu Lys Thr Gln Met Ile Tyr Gln Gln His Gln Ser
1
Trp Leu Arg Pro Val Leu Arg Ser Asn Arg Val Glu Tyr Cys Trp Cys Asn Ser Gly

Arg Ala Gln Cys His Ser Val Pro Val Lys Ser Cys Ser Glu Pro Arg Cys Phe Asn
                                          50
Gly Gly Thr Cys Gln Gln Ala Leu Tyr Phe Ser Asp Phe Val Cys Gln Cys Pro Glu

Gly Phe Ala Gly Lys Cys Cys Glu Ile Asp Thr Arg Ala Thr Cys Tyr Glu Asp Gln

Gly Ile Ser Tyr Arg Gly Thr Trp Ser Thr Ala Glu Ser Gly Ala Glu Cys Thr Asn Trp
                    100
Asn Ser Ser Ala Leu Ala Gln Lys Pro Tyr Ser Gly Arg Arg Pro Asp Ala Ile Arg

Leu Gly Leu Gly Asn His Asn Tyr Cys Arg Asn Pro Asp Arg Asp Ser Lys Pro Trp
                                                      150
Cys Tyr Val Phe Lys Ala Gly Lys Tyr Ser Ser Glu Phe Cys Ser Thr Pro Ala Cys

Ser Glu Gly Asn Ser Asp Cys Tyr Phe Gly Asn Gly Ser Ala Tyr Arg Gly Thr His

Ser Leu Thr Glu Ser Gly Ala Ser Cys Leu Pro Trp Asn Ser Met Ile Leu Ile Gly Lys
                        200
Val Tyr Thr Ala Gln Asn Pro Ser Ala Gln Ala Leu Gly Leu Gly Lys His Asn Tyr

Cys Arg Asn Pro Asp Gly Asp Ala Lys Pro Trp Cys His Met Leu Lys Asn Arg Arg
                                                          250
Leu Thr Trp Glu Tyr Cys Asp Val Pro Ser Cys Ser Thr Cys Gly Leu Arg Gln Tyr

Ser Gln Pro Gln Phe Arg Ile Lys Gly Gly Leu Phe Ala Asp Ile Ala Ser His Pro Trp

Gln Ala Ala Ile Phe Ala Lys His Arg Arg Ser Pro Gly Glu Arg Phe Leu Cys Gly
                                          300
Gly Ile Leu Ile Ser Ser Cys Trp Ile Leu Ser Ala Ala His Cys Phe Gln Glu Arg Phe

Pro Pro His His Leu Thr Val Ile Leu Gly Arg Thr Tyr Arg Val Val Pro Gly Glu Glu

Glu Gln Lys Phe Glu Val Glu Lys Tyr Ile Val His Lys Glu Phe Asp Asp Asp Thr
    350
Tyr Asp Asn Asp Ile Ala Leu Leu Gln Leu Lys Ser Asp Ser Ser Arg Cys Ala Gln

Glu Ser Ser Val Val Arg Thr Val Cys Leu Pro Pro Ala Asp Leu Gln Leu Pro Asp
                                          400
Trp Thr Glu Cys Glu Leu Ser Gly Tyr Gly Lys His Glu Ala Leu Ser Pro Phe Tyr

Ser Glu Arg Leu Lys Glu Ala His Val Arg Leu Tyr Pro Ser Ser Arg Cys Thr Ser

Gln His Leu Leu Asn Arg Thr Val Thr Asp Asn Met Leu Cys Ala Gly Asp Thr Arg
                        450
Ser Gly Gly Pro Gln Ala Asn Leu His Asp Ala Cys Gln Gly Asp Ser Gly Gly Pro

Leu Val Cys Leu Asn Asp Gly Arg Met Thr Leu Val Gly Ile Ile Ser Trp Gly Leu
                                                          500
Gly Cys Gly Gln Lys Asp Val Pro Gly Val Tyr Thr Lys Val Thr Asn Tyr Leu Asp

Trp Ile Arg Asp Asn Met Arg Pro
             527

* Site of cleavage in one-chain t-PA to give two-chain t-PA, in which the A-chain contains the two kringle regions and the B-chain contains the serine protease region.

METHOD OF ADMINISTERING TISSUE PLASMINOGEN ACTIVATOR

This is a continuation of application Ser. No. 07/831,641, filed Feb. 7, 1992 which is a continuation of Ser. No. 07/367,857 filed Jun. 19, 1989, both now abandoned.

The present invention relates to the formulation and administration of tissue plasminogen activator (t-PA).

There exists a dynamic equilibrium between the enzyme system capable of forming blood clots, the coagulation system, and the enzyme system capable of dissolving blood clots, the fibrinolytic system, which maintains an intact patent vascular bed. To limit loss of blood from injury, blood clots are formed in the injured vessel. After natural repair of the injury, the superfluous blood clots are dissolved through operation of the fibrinolytic system. Occasionally, blood clots form without traumatic injury and may lodge in major blood vessels resulting in a partial or even total obstruction of blood flow. When this occurs in the heart, lung or brain, the result may be a myocardial infarction, pulmonary embolism or stroke. These conditions combined are the leading cause of morbidity and mortality in the industrialised nations.

Blood clots consist of a fibrous network that is capable of dissolution by the proteolytic enzyme plasmin. The enzyme is derived from the inactive proenzyme, plasminogen, a component of blood plasma, by the action of a plasminogen activator. There are two immunologically distinct mammalian plasminogen activators. Intrinsic plasminogen activator, also known as urokinase, is an enzyme produced by the kidney and can be isolated from urine. It can also be prepared from a number of tissue culture sources. Extrinsic plasminogen activator, also known as vascular plasminogen activator and as tissue plasminogen activator (t-PA), can be isolated from many tissue homogenates (notably human uterus), the vascular cell wall and from some cell cultures. In addition to these two kinds of plasminogen activator, there is also a bacterial product, streptokinase, prepared from beta-haemolytic streptococci. A major drawback with both urokinase and streptokinase is that they are active throughout the circulation and not just at the site of a blood clot. They can, for example, destroy other blood proteins, such as fibrinogen, prothrombin, factor V and factor VIII so reducing blood clotting ability and increasing the risk of haemorrhage. In contrast, the biological activity of t-PA is dependent on the presence of fibrin to which it binds and where it is activated. Maximum activity is thus developed only at the site of a blood clot, i.e. in the presence of the fibrin network to be dissolved, and this greatly reduces the risk of haemorrhage.

t-PA is being increasingly used clinically, particularly in the treatment of acute myocardial infarction. Hitherto, t-PA has generally been administered by a small bolus injection followed by a continuous infusion. A typical protocol for treatment with t-PA is as follows:
 Initial bolus injection (about 10% of the lytic dose) over a period of 1-2 minutes
 High level lytic infusion for 1 hour
 Low level maintenance infusion for 2-3 hours.

Bolus injections have also been used in pharmacodynamic studies of the plasma concentration of t-PA (see for example Nilsson et al, Scand. J. Haematol., 33, 49–53 (1984)). However, such studies have indicated that the half life of t-PA in the circulation is less than 5 minutes and it has generally been assumed that most of the dose of t-PA must be administered by continuous infusion in order to maintain adequate concentrations of t-PA in the circulation to achieve thrombolysis. Studies in animals have also suggested that bolus injection has no advantages as a method of administration for t-PA (see for example Gold et al, Circulation, 77(3), 670–677 (1988)).

It has recently been suggested that t-PA and pro-urokinase are complementary in their mode of action and that a combined therapy using the two thrombolytic agents may have advantages. The specific combination was suggested of a bolus injection of t-PA followed by a infusion of pro-urokinase (Gurewich, Journal of the American College of Cardiology, Volume 10 No. Nov. 5, 1987, 16B–21B).

There has not been any suggestion in the case of thrombolytic therapy with t-PA alone that the whole of the dose of t-PA required to achieve thrombolysis should be administered as one or more bolus injections.

There is a continuing need to improve the administration of t-PA particularly in terms of speed and convenience of administration. It has now been found that t-PA can be administered as one or more bolus injections without the need for a following continuous infusion and that this mode of administration shows advantages over modes of administration involving continuous infusion. Despite the fact that the half life of t-PA is about 5 minutes and it is rapidly removed from the circulation, our results suggest that a thrombolytic effect can be produced which outlasts its circulating time.

The present invention provides a method for the treatment of a human being with a thrombotic disorder characterised in that t-PA is administered as a bolus injection of at least 7 MU of t-PA per injection.

The present invention also provides the use of t-PA for the manufacture of a medicament for the treatment of a thrombotic disorder by administering a bolus injection of at least 7 MU of t-PA per injection.

The use of a bolus injection for the administration of t-PA has a number of advantages over a continuous infusion.

In terms of ease of administration a single injection of low volume via a peripheral vein has considerable advantages over a continuous infusion that requires monitoring. Administration by bolus injection opens up the possibility that the thrombolytic agent t-PA may be administered at the point of first contact with the patient, e.g. in the home, either by paramedical personnel or casualty staff.

Administration by bolus injection also has advantages in terms of clinical efficacy. Thus the time to reperfusion may be minimised in comparison with an infusion, thereby reducing the time that the myocardium remains ischaemic. The optimal dose may well be lower with a bolus injection than that required when administration is by infusion thereby keeping bleeding complications to a minimum. In addition, the shorter duration of administration may well also reduce the dose-related bleeding thought to be associated with prolonged thrombolytic therapy.

When t-PA is administered by continuous infusion it is possible that the clinician may attempt to combine the administration of t-PA with the administration of other therapeutic substances in the same infusion and this may in turn change the bioavailability of the substances thus administered. Bolus injection of t-PA has the advantage that it avoids any possibility that the t-PA may be mixed with other therapeutic substances at the time of administration.

The dose of t-PA when administered by bolus injection may well be lower than the dose for administration by continuous infusion, in which case the cost per patient of therapy with t-PA would be minimised.

Finally administration of t-PA by means of a bolus injection has thrombolytic advantages. The higher blood levels achieved over a short period when the bolus is administered may cause the clot to be saturated with the thrombolytic agent resulting in faster lysis times than can be achieved by the relatively low concentrations administered by continuous infusion. The natural inhibitors of t-PA become rapidly saturated so that peak blood levels of free t-PA available for thrombolysis are reached quickly. In addition the short half life of t-PA means that following a bolus injection high levels of circulating t-PA are not present for prolonged periods. This has the potential to limit intravenous interaction with other therapeutic substances administered for the management of myocardial infarction.

The t-PA of use according to the present invention may be any bioactive protein substantially corresponding to mammalian, and especially human, t-PA and includes forms with and without glycosylation. It may be one- or two-chain t-PA, or a mixture thereof, as described in EP-A-112 122, and, in the case of fully glycosylated human t-PA, has an apparent molecular weight as determined by polyacrylamide gel electrophoresis of about 70,000 and an isoelectric point of between 7.5 and 8.0. Preferably the t-PA has a specific activity of about 0.3 to 0.6 MU/mg. As used herein a unit (U) of t-PA activity is the International Unit of activity as defined by the WHO, National Institute for Biological Standards and Control, Holly Hill, Hampstead, London NW3 6RB, United Kingdom and determined by comparison with a standard preparation using a clot-lysis assay.

The amino acid sequence of t-PA preferably substantially corresponds to that set forth in FIG. 1. The sequence may thus be identical to that in FIG. 1 or may contain one or more amino acid deletions, substitutions, insertions, inversions or additions of allelic origin or otherwise, the resulting sequence having at least 80%, and preferably 90%, homology with the sequence in FIG. 1 and retaining essentially the same biological and immunological properties of the protein. In particular, the sequence may be identical to that in FIG. 1 or may be the same but with the amino acid in the 245th position from the serine N-terminus being valine instead of methionine, either sequence optionally being without any of the first three amino acids or optionally having an additional polypeptide N-terminal presequence of Gly-Ala-Arg.

The amino acid sequence set forth in FIG. 1 has 35 cysteine residues and thus the potential for forming 17 disulphide bridges. Based on analogy with other proteins whose structure has been determined in more detail, the postulated structure for the sequence (arising from disulphide bond formation) between the amino acid in the 90th position and the proline C-terminus is set forth in FIG. 2. The structure of the N-terminal region is less certain although some proposals have been put forward (Progress in Fibrinolysis, 6, 269-293 (1983); and Proc. Natl. Acad. Sci. 81, 5355-5359 (1984)). The most important features of the structure of t-PA are the two kringle regions (between the 93rd and the 173rd amino acids and between the 180th and 261st amino acids), which are responsible for the binding of the protein to fibrin, and the serine protease region, which comprises the major part of the B-chain and which is responsible for the activation of plasminogen. The amino acids of special significance in serine proteases are the catalytic triad, His/Asp/Ser. In t-PA these occur at the 322nd, the 371st and the 463rd positions. The disulphide bridge between the 264th and 395th cysteine amino acid residues is also important in that it holds together the A- and the B-chains in the two chain form of t-PA.

In FIGS. 1 and 2, the conventional one and three letter codes have been employed for the amino acid residues as follows:

| Asp | D | Aspartic acid |
|-----|---|---------------|
| Arg | R | Arginine |
| Val | V | Valine |
| Ser | S | Serine |
| Trp | W | Tryptophan |
| Leu | L | Leucine |
| Pro | P | Proline |
| Met | M | Methionine |
| Phe | F | Phenylalanine |
| Ala | A | Alanine |
| Cys | C | Cysteine |
| Thr | T | Threonine |
| Lys | K | Lysine |
| Ile | I | Isoleucine |
| Glu | E | Glutamic acid |
| Gln | Q | Glutamine |
| Tyr | Y | Tyrosine |
| Gly | G | Glycine |
| Asn | N | Asparagine |
| His | H | Histidine |

The t-PA may be obtained by any of the procedures described or known in the art. For example, it may be obtained from a normal or neoplastic cell line of the kind described in Biochimica et Biophysica Acta, 580, 140-153 (1979); EP-A-41 766; or EP-A-113 319. It is preferred, however, that t-PA is obtained from a cultured transformed or transfected cell line using recombinant DNA technology as described in, for example, EP-A-93 619; EP-A-117 059; EP-A-117060; EP-A-173 552; EP-A-174 835; EP-A-178 105; EP-A-225 177; EP-A-225 286; WO 86/01538; WO 86/05514; or WO86/05807. It is particularly preferred that Chinese hamster ovary (CHO) cells are used for the production of t-PA and are derived in the manner as described in Molecular and Cellular Biology, 5(7), 1750-1759 (1985). In this way, the cloned gene is cotransfected with the gene encoding dihydrofolate reductase (dhfr) into dhfr-CHO cells. Transformants expressing dhfr are selected on media lacking nucleosides and are exposed to increasing concentrations of methotrexate. The dhfr and t-PA genes are thus coamplified leading to a stable cell line capable of expressing high levels of t-PA.

The t-PA is preferably purified using any of the procedures described or known in the art, such as the procedures described in Biochimica et Biophysica Acta, 580, 140-153 (1979); J. Biol. Chem., 254(6), 1998-2003 (1979; ibid, 256(13), 7035-7041 (1981); Eur. J. Biochem., 132, 681-686 (1983); EP-A-41 766; EP-A-113 319; or GB-A-2 122 219. Following purification the t-PA is preferably lyophilized most preferably as described in GB-A-2 176 702.

The t-PA will generally be dissolved in a predetermined volume (say up to 10 ml per 25 MU of t-PA) of sterile water for injection or a suitable alternative carrier such as 5% dextrose. The dose required for bolus injection will then be withdrawn from this volume into a syringe.

In accordance with the invention t-PA is administered as one or more bolus injections of at least 7 MU of t-PA per injection. Preferably the t-PA is administered as a single bolus injection of at least 7 MU of t-PA, preferably at least 12.5 MU of t-PA, for example 25 to 75 MU or 25 to 50 MU of t-PA. The doses given herein are for an average weight human patient of say 70 to 80 kg.

The dose will be given into a peripheral vein for example over a period of 1 to 2 minutes either by direct injection or via an indwelling venous catheter. If given by direct injection into a peripheral vein direct pressure should normally be applied for at least 5 minutes after withdrawing the needle to ensure that haemostasis has occurred.

One particular advantage of administration by bolus injection is that t-PA can be presented in the form of a pre-filled syringe. This simplifies the mode of administration considerably and increases the speed with which thrombolysis can be initiated.

Accordingly the present invention also provides a prefilled syringe containing a unit dose of t-PA in a form suitable for bolus injection. The unit dose of t-PA will generally be at least 7 MU, preferably at least 12.5 MU, for example 25 to 75 MU or 25 to 50 MU. Such unit doses may also be used for a bolus formulation.

The invention is illustrated by the following Examples.

EXAMPLE 1

A clarified harvest of t-PA obtained from a cultured transformed CHO cell line which was derived using the procedure of Molecular and Cellular Biology, 5(7), 1750-1759 (1985), was purified chromatographically and the t-PA collected as an aqueous solution containing 0.17M sodium citrate and 0.01% (w/v) Tween 80 at a pH of 5.5. The pH of the solution was adjusted to 3.0 with hydrochloric acid and the resulting solution concentrated by ultrafiltration using an H-10 Cartridge (Amicon Ltd., Upper Hill, Stonehouse, Gloucestershire, England). The concentrated aqueous solution was further purified by applying it to a gel filtration column (Sephadex G-150; Pharmacia Biotechnology, Uppsala, Sweden) and eluting with 0.85% saline solution containing 0.01% (w/v) Tween 80 at a pH of 3.0. A highly more using a disposable artificial kidney. The t-PA was precipitated out of solution by increasing the pH to 5.5 with sodium hydroxide and maintaining the suspension at 4° C. for 2 hours. The t-PA was recovered by centrifugation at 4000 xg for 30 minutes at 4° C. The pellet of t-PA was redissolved in an aqueous solution of sodium chloride (0.85% w/v) containing 0.01% (w/v) Tween 80 and adjusted to pH 3.0 with hydrochloric acid. The volume of saline solution used was that required to give a concentration of t-PA between 7 MU/ml and 10 MU/ml. This solution of t-PA was diluted with further aqueous sodium chloride (0.85% w/v) containing 0.01% (w/v) Tween 80 and adjusted to pH 3.0 with hydrochloric acid, and also with sufficient of a solution of 10% (w/v) mannitol in the same acid saline solution to give final concentrations of 5 MU/ml of t-PA and 25 mg/ml of mannitol. The resulting solution was filter sterilized and dispensed in volumes of 5 ml into glass vials which were frozen at −35° C. A vacuum was applied at 0.05 Torr. After about 24 hours, the temperature was gradually increased to 5° C. and maintained at this temperature for 16 hours. It was then increased again to 25° C. and the vacuum increased to 0.02 Torr for a further 24 hours, after which the vials were sealed under a partial vacuum of 600 Torr of dry nitrogen.

The vials, containing 25 MU of t-PA each, can be used for the preparation of a solution suitable for bolus injection by dissolving the contents of the vial in 5 ml of pyrogen free water for injection Eur. Ph..

EXAMPLE 2

The administration of t-PA by bolus injection was compared with administration by continuous infusion in an open, randomized pilot study in patients with acute myocardial infarction as defined by characteristic pain and ECG changes. Patients were entered into the study up to six hours after the onset of continuous chest pain. Patients were randomized to receive one or other of the following treatment regimes:

(i) INFUSION—An infusion of 50 MU t-PA over the first 1.5 hours followed by an infusion of a reduced rate of 5 MU per hour for the next 5 hours even if reperfusion is obtained, (ii) BOLUS INJECTION—4 Bolus injections of 12.5 MU (each over a period of 2 minutes) at 0, 20, 40 and 60 minutes, purified solution of t-PA was thus obtained which was concentrated once.

Perfusion grade of the infarct related coronary artery was assessed by coronary arteriography before and at intervals of 15, 35, 55 and 90 minutes after drug administration had commenced. Patency of the artery was assessed over 24 hours by continuous beat-to-beat monitoring of ST segment level and by recatheterization at 24 hours.

The t-PA was produced in accordance with the procedure of Example 1 and was provided as a white lyophilized powder in glass vials, each vial containing 25 MU of t-PA. For administration to patients the contents of a vial were dissolved in 5 ml of pyrogen-free water for injection Eur. Ph.. For continuous infusion the solution was further diluted with normal saline or 5% dextrose and used immediately. For bolus injection half of the volume (2.5 ml containing 12.5 MU of t-PA) was used at the first time point and the other half at the immediately subsequent time point.

Both groups of patients were given an intravenous bolus dose of 5000 IU heparin at the start of cardiac catheterization when the arterial sheath was in place. A continuous intravenous infusion of 1000 IU heparin per hour was started immediately after the 90 minute arteriogram and varied to accomplish an aPTT of 1.5 to 2.0 times normal (laboratory values), and maintained until 4 to 6 hours before removal of arterial and venous sheaths.

Reperfusion was assessed on the scale TIMI grades 0 to 3 (0=occluded, 3=complete recanalization). Results on 16 patients (8 in each group) were as follows:

BOLUS GROUP (n=8)

⅞ reached TIMI grade 3 at 90 minutes
⅛ failed to recanalize
2/8 late reocclusion at 24 hours
Mean time to reperfusion—22.4 minutes.

INFUSION GROUP (n=8)

⅝ reached TIMI grade 3 at 90 minutes
⅜ failed to recanalize

2/8 recanalized late at 24 hours
Mean time to reperfusion—39.6 minutes.

I claim:

1. A method for the treatment of a human being with a thrombotic disorder wherein t-PA, having the amino acid sequence set forth in FIG. 1 or an amino acid sequence that is at least 90% homologous with that set forth in FIG. 1, is administered by direct injection into a peripheral vein to the human being as a serial bolus injection of at least 25 MU of t-PA per injection.

2. A method according to claim 1, wherein t-PA has the amino acid sequence set forth in FIG. 1 or has the same amino acid sequence both the amino acid in the 245th position from the serine N-terminus being valine instead of methionine.

3. A method according to claim 1 or claim 2, wherein the thrombotic disorder is a myocardial infarction.

4. A method according to claim 1, wherein the amount of t-PA per injection is from 25 to 75 MU.

5. A method according to claim 4, wherein the amount of t-PA per injection is from 25 to 50 MU.

6. A method for the treatment of a human being with a thrombotic disorder wherein an aqueous solution consisting essentially of t-PA, having the amino acid sequence set forth in FIG. 1 or an amino acid sequence that is at least 90% homologous with that set forth in FIG. 1, dissolved in said aqueous solution is administered by direct injection into a peripheral vein to the human being as a serial bolus injection of at least 25 MU of t-PA per injection.

7. A method according to claim 6 wherein the aqueous solution is said t-PA dissolved in sterile water for injection or pyrogen-free water for injection.

8. A method according to claim 7, wherein the aqueous solution also contains dextrose.

* * * * *

UNITED STATES PATENT AND TRADEMARK OFFICE
CERTIFICATE OF CORRECTION

PATENT NO. : 5,342,616
DATED : August 30, 1994
INVENTOR(S) : COHEN

It is certified that error appears in the above-identified patent and that said letters patent is hereby corrected as shown below:

On the title page;
Item [73] should read:

[73] Assignee Burroughs Wellcome Co.

Signed and Sealed this

Seventh Day of February, 1995

*Attest:*

BRUCE LEHMAN

*Attesting Officer*      *Commissioner of Patents and Trademarks*